(12) United States Patent
Zentgraf et al.

(10) Patent No.: US 9,044,221 B2
(45) Date of Patent: Jun. 2, 2015

(54) EXCHANGEABLE SYSTEM FOR MINIMALLY INVASIVE BEATING HEART REPAIR OF HEART VALVE LEAFLETS

(75) Inventors: John Zentgraf, Minneapolis, MN (US); David Joseph Parins, Corcoran, MN (US); Arun Saini, Burnsville, MN (US)

(73) Assignee: NeoChord, Inc., Minnetonka, MN (US)

( * ) Notice: Subject to any disclaimer, the term of this patent is extended or adjusted under 35 U.S.C. 154(b) by 142 days.

(21) Appl. No.: 13/339,865

(22) Filed: Dec. 29, 2011

(65) Prior Publication Data

US 2012/0184971 A1    Jul. 19, 2012

Related U.S. Application Data

(60) Provisional application No. 61/428,048, filed on Dec. 29, 2010.

(51) Int. Cl.
*A61B 17/04* (2006.01)
*A61B 1/018* (2006.01)
(Continued)

(52) U.S. Cl.
CPC ........... *A61B 17/0469* (2013.01); *A61B 5/0084* (2013.01); *A61B 17/0483* (2013.01); *A61B 17/06114* (2013.01); *A61B 2017/00057* (2013.01); *A61B 2017/00199* (2013.01); (Continued)

(58) Field of Classification Search
CPC ........... A61B 17/3494; A61B 17/0469; A61B 2017/3484–2017/3488; A61M 25/0625; A61M 2025/0006
USPC .......................... 606/108, 139–150; 623/1.11
See application file for complete search history.

(56) References Cited

U.S. PATENT DOCUMENTS 2,751,908 A    6/1956  Wallace
3,667,474 A    6/1972  Lapkin
(Continued)

FOREIGN PATENT DOCUMENTS

EP    1039851    7/2005
EP    1637091    3/2006
(Continued)

OTHER PUBLICATIONS

Notification of International Search Report and Written Opinion of the International Searching Authority, Application No. PCT/US2011/067884, mailed Jul. 30, 2012, 11 pages.
(Continued)

*Primary Examiner* — Katherine Dowe
*Assistant Examiner* — Jonathan Hollm
(74) *Attorney, Agent, or Firm* — Patterson Thuente Pedersen, P.A.

(57) ABSTRACT

Improved methods and apparatuses for heart valve repair in a beating heart of a patient utilize an exchangeable heart valve repair system. Heart valve repair system can include a port adapted to be seated in the heart wall and an imaging catheter slidable within the port. The imaging catheter can be selectively locked relative to the port for insertion into the heart and unlocked once the port is seated to allow the imaging catheter to move distally towards target tissue. A deployment catheter slidably disposed in the imaging catheter and a repair cartridge slidably disposed in the deployment catheter can be used to capture the target tissue and deploy a repair device into the tissue after proper capture is confirmed. System elements can be selectively removed from and replaced within port to deploy additional repair devices while port maintains a seal while elements are and are not inserted.

21 Claims, 14 Drawing Sheets

(51) Int. Cl.
*A61B 1/04* (2006.01)
*A61B 1/313* (2006.01)
*A61B 5/00* (2006.01)
*A61B 17/06* (2006.01)
*A61B 17/00* (2006.01)
*A61B 17/34* (2006.01)
*A61M 37/00* (2006.01)
*A61M 39/06* (2006.01)
*A61B 1/00* (2006.01)

(52) U.S. Cl.
CPC ........... *A61B2017/00278* (2013.01); *A61B 2017/00296* (2013.01); *A61B 2017/003* (2013.01); *A61B 2017/00349* (2013.01); *A61B 2017/0042* (2013.01); *A61B 2017/00477* (2013.01); *A61B 2017/00783* (2013.01); *A61B 2017/00876* (2013.01); *A61B 2017/0409* (2013.01); *A61B 2017/0417* (2013.01); *A61B 2017/3419* (2013.01); *A61B 2017/349* (2013.01); *A61M 37/0015* (2013.01); *A61M 2039/064* (2013.01); *A61M 2039/0653* (2013.01); *A61B 1/00165* (2013.01); *A61B 1/018* (2013.01); *A61B 1/04* (2013.01); *A61B 1/3137* (2013.01); *A61B 5/0044* (2013.01); *A61B 2017/3425* (2013.01)

(56) References Cited

U.S. PATENT DOCUMENTS

| | | |
|---|---|---|
| 3,744,062 A | 7/1973 | Parsonnet |
| 3,842,840 A | 10/1974 | Schweizer |
| 4,258,716 A | 3/1981 | Sutherland |
| 4,351,345 A | 9/1982 | Carney |
| 4,935,027 A | 6/1990 | Yoon |
| 4,957,498 A | 9/1990 | Caspari et al. |
| 4,960,424 A | 10/1990 | Grooters |
| 4,967,498 A | 11/1990 | Kao |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth |
| 5,336,229 A | 8/1994 | Noda |
| 5,383,877 A | 1/1995 | Clarke |
| 5,431,666 A | 7/1995 | Sauer |
| 5,433,723 A * | 7/1995 | Lindenberg et al. ........... 606/198 |
| 5,452,733 A | 9/1995 | Sterman |
| 5,474,519 A | 12/1995 | Bloomer |
| 5,547,455 A | 8/1996 | McKenna |
| 5,556,411 A * | 9/1996 | Taoda et al. .................... 606/185 |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo |
| 5,665,100 A | 9/1997 | Yoon |
| 5,667,472 A | 9/1997 | Finn |
| 5,667,473 A | 9/1997 | Finn |
| 5,667,478 A | 9/1997 | McFarlin |
| 5,693,091 A | 12/1997 | Larson |
| 5,728,113 A | 3/1998 | Sherts |
| 5,762,458 A | 6/1998 | Wang |
| 5,762,613 A | 6/1998 | Sutton |
| 5,766,163 A * | 6/1998 | Mueller et al. ................... 606/7 |
| 5,772,597 A | 6/1998 | Goldberger |
| 5,772,672 A | 6/1998 | Toy |
| 5,785,658 A | 7/1998 | Benaron |
| 5,797,960 A | 8/1998 | Stevens |
| 5,830,231 A | 11/1998 | Geiges |
| 5,839,639 A | 11/1998 | Sauer |
| 5,897,564 A | 4/1999 | Schulze |
| 5,908,428 A | 6/1999 | Scirica |
| 5,908,429 A * | 6/1999 | Yoon .............................. 606/144 |
| 5,919,128 A | 7/1999 | Fitch |
| 5,961,440 A | 10/1999 | Schweich |
| 5,972,004 A | 10/1999 | Williamson |
| 5,972,030 A | 10/1999 | Garrison |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels |
| 6,045,497 A | 4/2000 | Schweich |
| 6,050,936 A | 4/2000 | Schweich |
| 6,053,933 A | 4/2000 | Balazs |
| 6,059,715 A | 5/2000 | Schweich |
| 6,077,214 A | 6/2000 | Mortier |
| 6,117,144 A | 9/2000 | Nobles |
| 6,129,683 A | 10/2000 | Sutton |
| 6,149,660 A | 11/2000 | Laufer |
| 6,152,934 A | 11/2000 | Harper |
| 6,162,168 A | 12/2000 | Schweich |
| 6,162,233 A | 12/2000 | Williamson |
| 6,165,119 A | 12/2000 | Schweich |
| 6,165,120 A | 12/2000 | Schweich |
| 6,165,183 A | 12/2000 | Kuehn |
| 6,178,346 B1 | 1/2001 | Amundson |
| 6,183,411 B1 | 2/2001 | Mortier |
| 6,190,357 B1 | 2/2001 | Ferrari |
| 6,234,079 B1 | 5/2001 | Chertkow |
| 6,234,995 B1 | 5/2001 | Peacock |
| 6,245,079 B1 | 6/2001 | Nobles |
| 6,260,552 B1 | 7/2001 | Mortier |
| 6,261,222 B1 | 7/2001 | Schweich |
| 6,264,602 B1 | 7/2001 | Mortier |
| 6,269,819 B1 | 8/2001 | Oz |
| 6,270,508 B1 | 8/2001 | Klieman |
| 6,283,993 B1 | 9/2001 | Cosgrove |
| 6,312,447 B1 | 11/2001 | Grimes |
| 6,332,863 B1 | 12/2001 | Schweich |
| 6,332,864 B1 | 12/2001 | Schweich |
| 6,332,893 B1 | 12/2001 | Mortier |
| 6,355,050 B1 | 3/2002 | Andreas |
| 6,401,720 B1 | 6/2002 | Stevens |
| 6,402,679 B1 | 6/2002 | Mortier |
| 6,402,680 B2 | 6/2002 | Mortier |
| 6,402,781 B1 | 6/2002 | Langberg |
| 6,406,420 B1 | 6/2002 | McCarthy |
| 6,419,626 B1 | 7/2002 | Yoon |
| 6,436,107 B1 | 8/2002 | Wang |
| 6,443,922 B1 | 9/2002 | Roberts |
| 6,451,054 B1 | 9/2002 | Stevens |
| 6,461,366 B1 | 10/2002 | Seguin |
| 6,508,777 B1 | 1/2003 | Macoviak |
| 6,514,194 B2 | 2/2003 | Schweich |
| 6,533,796 B1 | 3/2003 | Sauer |
| 6,537,198 B1 | 3/2003 | Vidlund |
| 6,537,314 B1 | 3/2003 | Langberg |
| 6,551,331 B2 | 4/2003 | Nobles |
| 6,558,416 B2 | 5/2003 | Cosgrove |
| 6,562,052 B2 | 5/2003 | Nobles |
| 6,564,805 B2 | 5/2003 | Garrison |
| 6,582,388 B1 | 6/2003 | Coleman |
| 6,585,727 B1 | 7/2003 | Cashman |
| 6,589,160 B2 | 7/2003 | Schweich |
| 6,602,288 B1 | 8/2003 | Cosgrove |
| 6,616,684 B1 | 9/2003 | Vidlund |
| 6,619,291 B2 | 9/2003 | Hlavka |
| 6,622,730 B2 | 9/2003 | Ekvall |
| 6,626,917 B1 | 9/2003 | Craig |
| 6,626,930 B1 | 9/2003 | Allen |
| 6,629,534 B1 | 10/2003 | Dell |
| 6,629,921 B1 | 10/2003 | Schweich |
| 6,629,984 B1 | 10/2003 | Chan |
| 6,645,205 B2 | 11/2003 | Ginn |
| 6,679,268 B2 | 1/2004 | Stevens |
| 6,692,605 B2 | 2/2004 | Kerr et al. |
| 6,695,866 B1 | 2/2004 | Kuehn |
| 6,709,456 B2 | 3/2004 | Langberg |
| 6,718,985 B2 | 4/2004 | Hlavka |

(56) References Cited

U.S. PATENT DOCUMENTS

| | | | |
|---|---|---|---|
| 6,723,038 B1 | 4/2004 | Schroeder | |
| 6,726,648 B2 * | 4/2004 | Kaplon et al. ............ 604/9 |
| 6,733,509 B2 | 5/2004 | Nobles | |
| 6,740,107 B2 | 5/2004 | Loeb | |
| 6,746,471 B2 | 6/2004 | Mortier | |
| 6,752,713 B2 | 6/2004 | Johnsons | |
| 6,752,813 B2 | 6/2004 | Goldfarb | |
| 6,755,777 B2 | 6/2004 | Schweich | |
| 6,764,510 B2 | 7/2004 | Vidlund | |
| 6,770,083 B2 | 8/2004 | Seguin | |
| 6,770,084 B1 | 8/2004 | Bain | |
| 6,793,618 B2 | 9/2004 | Schweich | |
| 6,802,860 B2 | 10/2004 | Cosgrove | |
| 6,808,488 B2 | 10/2004 | Mortier | |
| 6,810,882 B2 | 11/2004 | Langberg | |
| 6,840,246 B2 | 1/2005 | Downing | |
| 6,858,003 B2 | 2/2005 | Evans | |
| 6,875,224 B2 | 4/2005 | Grimes | |
| 6,893,448 B2 | 5/2005 | O'Quinn | |
| 6,908,424 B2 | 6/2005 | Mortier | |
| 6,918,917 B1 | 7/2005 | Nguyen | |
| 6,921,407 B2 | 7/2005 | Nguyen | |
| 6,929,715 B2 | 8/2005 | Fladda | |
| 6,936,054 B2 | 8/2005 | Chu | |
| 6,955,175 B2 | 10/2005 | Stevens | |
| 6,962,605 B2 | 11/2005 | Cosgrove | |
| 6,978,176 B2 | 12/2005 | Lattouf | |
| 6,986,775 B2 | 1/2006 | Morales | |
| 6,989,028 B2 | 1/2006 | Lashinski | |
| 6,991,635 B2 | 1/2006 | Takamoto | |
| 6,997,950 B2 | 2/2006 | Chawla | |
| 7,004,176 B2 | 2/2006 | Lau | |
| 7,004,952 B2 | 2/2006 | Nobles | |
| 7,011,669 B2 | 3/2006 | Kimblad | |
| 7,044,905 B2 | 5/2006 | Vidlund | |
| 7,048,754 B2 | 5/2006 | Martin | |
| 7,077,862 B2 | 7/2006 | Vidlund | |
| 7,083,628 B2 | 8/2006 | Bachman | |
| 7,083,638 B2 | 8/2006 | Foerster | |
| 7,090,686 B2 | 8/2006 | Nobles | |
| 7,094,244 B2 | 8/2006 | Schreck | |
| 7,100,614 B2 | 9/2006 | Stevens | |
| 7,112,207 B2 | 9/2006 | Allen | |
| 7,112,219 B2 | 9/2006 | Vidlund | |
| 7,118,583 B2 | 10/2006 | O'Quinn | |
| 7,122,040 B2 | 10/2006 | Hill | |
| 7,179,291 B2 | 2/2007 | Rourke | |
| 7,186,264 B2 | 3/2007 | Liddicoat | |
| 7,189,199 B2 | 3/2007 | McCarthy | |
| 7,217,240 B2 | 5/2007 | Snow | |
| 7,226,467 B2 | 6/2007 | Lucatero | |
| 7,247,134 B2 | 7/2007 | Vidlund | |
| 7,250,028 B2 | 7/2007 | Julian | |
| 7,288,097 B2 | 10/2007 | Seguin | |
| 7,294,148 B2 | 11/2007 | McCarthy | |
| 7,381,210 B2 | 6/2008 | Zarbatany | |
| 7,464,712 B2 | 12/2008 | Oz | |
| 7,563,267 B2 | 7/2009 | Goldfarb | |
| 7,563,273 B2 | 7/2009 | Goldfarb | |
| 7,604,646 B2 | 10/2009 | Goldfarb | |
| 7,608,091 B2 | 10/2009 | Goldfarb | |
| 7,635,386 B1 * | 12/2009 | Gammie ............ 623/2.11 |
| 7,666,204 B2 | 2/2010 | Thornton | |
| 7,815,654 B2 | 10/2010 | Chu | |
| 7,879,048 B2 | 2/2011 | Bain | |
| 7,887,552 B2 | 2/2011 | Bachman | |
| 8,465,500 B2 | 6/2013 | Speziali | |
| 2001/0005787 A1 | 6/2001 | Oz | |
| 2001/0016675 A1 | 8/2001 | Mortier | |
| 2001/0021872 A1 | 9/2001 | Bailey | |
| 2002/0013571 A1 | 1/2002 | Goldfarb | |
| 2002/0029080 A1 | 3/2002 | Mortier | |
| 2002/0049402 A1 | 4/2002 | Peacock | |
| 2002/0077524 A1 | 6/2002 | Schweich | |
| 2002/0169359 A1 | 11/2002 | McCarthy | |
| 2002/0173694 A1 | 11/2002 | Mortier | |
| 2002/0183766 A1 | 12/2002 | Seguin | |
| 2003/0004562 A1 | 1/2003 | DiCarlo | |
| 2003/0032979 A1 | 2/2003 | Mortier | |
| 2003/0050529 A1 | 3/2003 | Vidlund | |
| 2003/0050693 A1 | 3/2003 | Quijano et al. | |
| 2003/0078600 A1 | 4/2003 | O'Quinn | |
| 2003/0105519 A1 | 6/2003 | Fasol | |
| 2003/0130731 A1 | 7/2003 | Vidlund | |
| 2003/0166992 A1 | 9/2003 | Schweich | |
| 2003/0167071 A1 | 9/2003 | Martin et al. | |
| 2003/0171641 A1 | 9/2003 | Schweich | |
| 2003/0181928 A1 | 9/2003 | Vidlund | |
| 2003/0187457 A1 | 10/2003 | Weber | |
| 2003/0195529 A1 | 10/2003 | Takamoto | |
| 2003/0199975 A1 | 10/2003 | Gabbay | |
| 2004/0003819 A1 | 1/2004 | St. Goar | |
| 2004/0030382 A1 | 2/2004 | St. Goar | |
| 2004/0039442 A1 | 2/2004 | St. Goar | |
| 2004/0044350 A1 | 3/2004 | Martin | |
| 2004/0044365 A1 | 3/2004 | Bachman | |
| 2004/0049207 A1 | 3/2004 | Goldfarb | |
| 2004/0049552 A1 | 3/2004 | Motoyama | |
| 2004/0087975 A1 | 5/2004 | Lucatero | |
| 2004/0087978 A1 | 5/2004 | Velez et al. | |
| 2004/0092962 A1 | 5/2004 | Thornton | |
| 2004/0097805 A1 * | 5/2004 | Verard et al. ............ 600/428 |
| 2004/0116767 A1 | 6/2004 | Hermann | |
| 2004/0122448 A1 | 6/2004 | Levine | |
| 2004/0127983 A1 | 7/2004 | Mortier | |
| 2004/0133063 A1 | 7/2004 | McCarthy | |
| 2004/0167374 A1 | 8/2004 | Schweich | |
| 2004/0167539 A1 | 8/2004 | Kuehn | |
| 2004/0225300 A1 | 11/2004 | Goldfarb | |
| 2004/0225304 A1 | 11/2004 | Vidlund | |
| 2004/0236353 A1 | 11/2004 | Bain | |
| 2004/0236354 A1 | 11/2004 | Seguin | |
| 2004/0243229 A1 | 12/2004 | Vidlund | |
| 2004/0267083 A1 | 12/2004 | McCarthy | |
| 2005/0004668 A1 | 1/2005 | Aklog et al. | |
| 2005/0021055 A1 | 1/2005 | Toubia | |
| 2005/0021056 A1 | 1/2005 | St. Goar | |
| 2005/0021057 A1 | 1/2005 | St. Goar | |
| 2005/0033446 A1 | 2/2005 | Deem | |
| 2005/0044365 A1 | 2/2005 | Bachman | |
| 2005/0049667 A1 * | 3/2005 | Arbefeuille et al. ....... 623/1.11 |
| 2005/0065396 A1 | 3/2005 | Mortier | |
| 2005/0075723 A1 | 4/2005 | Schroeder | |
| 2005/0075727 A1 | 4/2005 | Wheatley | |
| 2005/0101975 A1 | 5/2005 | Nguyen | |
| 2005/0125011 A1 | 6/2005 | Spence | |
| 2005/0131277 A1 | 6/2005 | Schweich | |
| 2005/0131533 A1 | 6/2005 | Alfieri | |
| 2005/0143620 A1 | 6/2005 | Mortier | |
| 2005/0148815 A1 | 7/2005 | Mortier | |
| 2005/0149014 A1 | 7/2005 | Hauck | |
| 2005/0154402 A1 | 7/2005 | Sauer | |
| 2005/0165419 A1 | 7/2005 | Sauer | |
| 2005/0171601 A1 | 8/2005 | Cosgrove | |
| 2005/0216039 A1 | 9/2005 | Lederman | |
| 2005/0240202 A1 | 10/2005 | Shennib | |
| 2005/0251187 A1 | 11/2005 | Beane | |
| 2006/0020275 A1 | 1/2006 | Goldfarb et al. | |
| 2006/0036317 A1 | 2/2006 | Vidlund | |
| 2006/0041306 A1 | 2/2006 | Vidlund | |
| 2006/0052868 A1 | 3/2006 | Mortier | |
| 2006/0058871 A1 | 3/2006 | Zakay | |
| 2006/0074484 A1 | 4/2006 | Huber | |
| 2006/0074485 A1 | 4/2006 | Realyvasquez | |
| 2006/0089671 A1 | 4/2006 | Goldfarb | |
| 2006/0100699 A1 | 5/2006 | Vidlund | |
| 2006/0127509 A1 | 6/2006 | Eckman | |
| 2006/0135993 A1 | 6/2006 | Seguin | |
| 2006/0149123 A1 | 7/2006 | Vidlund | |
| 2006/0161040 A1 | 7/2006 | McCarthy | |
| 2006/0161193 A1 | 7/2006 | Beane | |
| 2006/0184203 A1 | 8/2006 | Martin | |
| 2006/0195012 A1 | 8/2006 | Mortier | |
| 2006/0195134 A1 | 8/2006 | Crittenden | |

(56) References Cited

U.S. PATENT DOCUMENTS

| | | |
|---|---|---|
| 2006/0195183 A1 | 8/2006 | Navia et al. |
| 2006/0241340 A1 | 10/2006 | Schroeder |
| 2006/0287657 A1 | 12/2006 | Bachman |
| 2007/0002627 A1 | 1/2007 | Youn |
| 2007/0027451 A1 | 2/2007 | Desinger |
| 2007/0049952 A1 | 3/2007 | Weiss |
| 2007/0050022 A1 | 3/2007 | Vidlund |
| 2007/0055303 A1 | 3/2007 | Vidlund |
| 2007/0088375 A1 | 4/2007 | Beane |
| 2007/0100356 A1 | 5/2007 | Lucatero |
| 2007/0112244 A1 | 5/2007 | McCarthy |
| 2007/0118154 A1 | 5/2007 | Crabtree |
| 2007/0118155 A1 | 5/2007 | Goldfarb |
| 2007/0129737 A1 | 6/2007 | Goldfarb |
| 2007/0179511 A1 | 8/2007 | Paolitto |
| 2007/0197858 A1 | 8/2007 | Goldfarb |
| 2007/0203391 A1 | 8/2007 | Bloom |
| 2007/0232941 A1 | 10/2007 | Rabinovich |
| 2007/0239272 A1 | 10/2007 | Navia |
| 2007/0265643 A1 | 11/2007 | Beane |
| 2007/0299468 A1 | 12/2007 | Viola |
| 2008/0027468 A1 | 1/2008 | Fenton |
| 2008/0051703 A1 | 2/2008 | Thornton |
| 2008/0065011 A1 | 3/2008 | Marchand |
| 2008/0065156 A1 | 3/2008 | Hauser |
| 2008/0065205 A1 | 3/2008 | Nguyen |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb |
| 2008/0167714 A1 | 7/2008 | St. Goar |
| 2008/0183194 A1 | 7/2008 | Goldfarb |
| 2008/0188873 A1* | 8/2008 | Speziali .................. 606/144 |
| 2008/0195200 A1 | 8/2008 | Vidlund |
| 2008/0208006 A1 | 8/2008 | Farr |
| 2008/0228223 A1 | 9/2008 | Alkhatib |
| 2009/0082857 A1 | 3/2009 | Lashinski et al. |
| 2009/0105729 A1* | 4/2009 | Zentgraf .................. 606/139 |
| 2009/0105751 A1 | 4/2009 | Zentgraf |
| 2009/0131880 A1 | 5/2009 | Speziali |
| 2009/0156995 A1 | 6/2009 | Martin |
| 2009/0163934 A1 | 6/2009 | Raschdorf |
| 2009/0259304 A1 | 10/2009 | O'Beirne |
| 2010/0042147 A1 | 2/2010 | Janovsky et al. |
| 2010/0160726 A1 | 6/2010 | Windheuser |
| 2010/0174297 A1 | 7/2010 | Speziali |
| 2014/0039324 A1 | 2/2014 | Speziali |

FOREIGN PATENT DOCUMENTS

| | | |
|---|---|---|
| EP | 1845861 A2 | 10/2007 |
| EP | 1408850 | 9/2009 |
| EP | 1845861 | 11/2009 |
| JP | 06142114 | 5/1994 |
| WO | WO 99/00059 | 1/1999 |
| WO | WO 99/30647 | 6/1999 |
| WO | WO 00/06026 A2 | 2/2000 |
| WO | WO 00/06026 A3 | 2/2000 |
| WO | WO 00/06027 | 2/2000 |
| WO | WO 00/06028 | 2/2000 |
| WO | WO 00/16700 | 3/2000 |
| WO | WO 01/66018 | 9/2001 |
| WO | WO 01/95809 | 12/2001 |
| WO | WO 03/001893 | 1/2003 |
| WO | WO 03/059209 A2 | 7/2003 |
| WO | WO 03/082157 | 10/2003 |
| WO | WO 03/082158 | 10/2003 |
| WO | WO 2004/021893 A2 | 3/2004 |
| WO | WO 2004/043265 | 5/2004 |
| WO | WO 2005/039428 | 5/2005 |
| WO | WO 2005/094525 | 10/2005 |
| WO | WO 2006/012750 | 2/2006 |
| WO | WO 2006/032051 | 3/2006 |
| WO | WO 2006/065966 | 6/2006 |
| WO | WO 2006/078694 | 7/2006 |
| WO | WO 2006/116310 | 11/2006 |
| WO | WO 2006/127509 | 11/2006 |
| WO | WO 2007/002627 | 1/2007 |
| WO | WO 2007/027451 | 3/2007 |
| WO | WO 2007/062128 | 5/2007 |
| WO | WO 2007/081418 | 7/2007 |
| WO | WO 2007/117612 | 10/2007 |
| WO | WO 2008/010738 | 1/2008 |
| WO | WO 2009/052528 | 4/2009 |

OTHER PUBLICATIONS

European Search Report, EP Application No. 08839048.9, dated Sep. 16, 2010, 7 pages.

Written Opinion of the International Search Authority, International Application No. PCT/US2008/080560, Filed Oct. 20, 2008, Date of Completion: Aug. 24, 2009.

Port Access System for Mitral Valve Repair Proves Its Value in Study; MedGadget, Jul. 9, 2009 as available at: http://medgadget.com/archives/2009/07port access system for mitral valve repair proves its value in study.html (5 pages).

Interactive Cardio Vascular and Thoracic Surgery; Abstracts: Supplemental 3 to vol. 7 (Sep. 2008), 52 pages.

Application and File History for U.S. Appl. No. 11/813,695, filed Jul. 11, 2007, Inventor: Giovanni Speziali.

Application and File History for U.S. Appl. No. 12/254,808, filed Oct. 20, 2008, Inventor: John Zentfraf.

Application and File History for U.S. Appl. No. 12/709,220, filed Feb. 19, 2010, Inventor: Giovanni Speziali.

International Search Report, Application No. PCT/US2008/080560, dated Aug. 25, 2009, 3 pages.

International Search Report, Application No. PCT/US2008/080560, dated Aug. 28, 2009, 2 pages.

Application and File History for U.S. Appl. No. 12/254,807, filed Oct. 20, 2008, Inventor: John Zentgraf.

Extended European Search Report, Application No. EP 06718728.6, Dated Nov. 11, 2009.

PCT Search Report and Written Opinion, Application No. PCT/US06/01699, mailed May 6, 2008.

International Preliminary Report on Patentability, Application No. PCT/US2011/067884, mailed Jul. 11, 2013, 5 pages.

PCT International Preliminary Report on Patentability for PCT/US2008/080560, dated Apr. 29, 2010, 7 pages.

Application and File History for U.S. Appl. No. 13/898,709, filed May 21, 2013. Inventors: Speziali.

Application and File History for U.S. Appl. No. 13/340,185, filed Dec. 29, 2011. Inventors: Zentgraf et al.

US 6,197,052, 03/2001, Cosgrove (withdrawn)

* cited by examiner

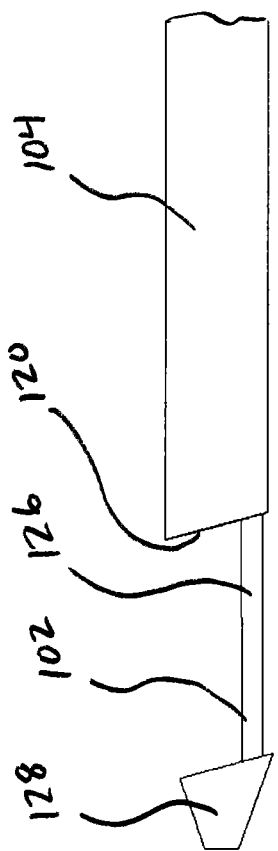

EXCHANGEABLE SYSTEM FOR MINIMALLY INVASIVE BEATING HEART REPAIR OF HEART VALVE LEAFLETS

RELATED APPLICATION

The present application claims the benefit of U.S. Provisional Application No. 61/428,048 filed Dec. 29, 2010, which is incorporated herein in its entirety by reference.

FIELD OF THE INVENTION

The present invention relates to minimally invasive repair of a heart valve. More particularly, the present invention relates to minimally invasive repair of heart valves utilizing an exchangeable system that allows for multiple repair devices to be deployed with a single access into the heart that permit the repairs to be done on a beating heart without the need for cardiopulmonary bypass and open heart access to the heart.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into a position accessible through the sternotomy. An opening, or atriotomy, is then made in the left atrium, anterior to the right pulmonary veins. The atriotomy is retracted by means of sutures or a retraction device, exposing the mitral valve directly posterior to the atriotomy. One of the aforementioned techniques may then be used to repair or replace the valve.

An alternative technique for mitral valve access may be used when a median sternotomy and/or rotational manipulation of the heart are/is undesirable. In this technique, a large incision is made in the right lateral side of the chest, usually in the region of the fifth intercostal space. One or more ribs may be removed from the patient, and other ribs near the incision are retracted outward to create a large opening onto the thoracic cavity. The left atrium is then exposed on the posterior side of the heart, and an atriotomy is formed in the wall of the left atrium, through which the mitral valve may be accessed for repair or replacement.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae result in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This operation is generally carried out through a median sternotomy and requires cardiopulmonary bypass with aortic cross-clamp and cardioplegic arrest of the heart.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

One alternative to open heart surgery is a robotically guided, thoracoscopically assisted cardiotomy procedure marketed under the tradename of the DaVinci® system. Instead of requiring a sternotomy, the DaVinci® system uses a minimally invasive approach guided by camera visualization and robotic techniques. Unfortunately, the DaVinci® system is not approved for mitral valve repair procedures on a beating heart. Thus, the use of the DaVinci® system for mitral valve repair still requires a cardiopulmonary bypass with aortic cross-clamp and cardioplegic arrest of the heart.

While there are other laparoscopic and minimally invasive surgical techniques and tools that have been developed, most of these devices are not useable for the unique requirements of mitral valve repair on a beating heart. Suturing devices like the Superstich™ vascular suturing device or the Gore® suture passer are designed to permit manual placement of sutures as part of a surgical procedure, but are not designed for use on a beating heart. While certain annuloplasty techniques and instruments that can suture an annuloplasty ring as part of vascular repair or heart bypass surgery may be used in conjunction with a beating heart, these annuloplasty procedures do not involve the capture or retention of a constantly moving leaflet. Consequently, the design and use of annuloplasty techniques and instruments are of little help in solving the problems of developing instruments and techniques for minimally invasive thoracoscopic repair of heart valves.

Recently, a technique has been developed for minimally invasive thoracoscopic repair of heart valves while the heart is still beating. PCT Pub. No. WO 2006/078694 A2 to Speziali discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. U.S. Publication No. 2008/0228223 to Alkhatib also discloses a similar apparatus for attaching a prosthetic tether between a leaflet of a patient's heart valve and another portion of the patient's heart to help prevent prolapse of the leaflet and/or to otherwise improve leaflet function.

More recent versions of these techniques are disclosed in U.S. Patent Application Publication Nos. 2009/0105751 and 2009/0105729 to Zentgraf, which disclose an integrated device that can enter the heart chamber, navigate to the leaflet, capture the leaflet, confirm proper capture, and deliver a suture as part of a mitral valve regurgitation (MR) repair.

While the Speziali and Zentgraf techniques represent a significant advance over open heart techniques and previous minimally invasive techniques for heart valve repair, it would be advantageous to further improve upon these techniques.

SUMMARY OF THE INVENTION

Improved methods and apparatuses for heart valve repair in a beating heart of a patient utilize an exchangeable heart valve repair system. Heart valve repair system can include a port adapted to be seated in the heart wall and an imaging catheter slidable within the port. The imaging catheter can be selectively locked relative to the port for insertion into the heart and unlocked once the port is seated to allow the imaging catheter to move distally towards target tissue. A deployment catheter slidably disposed in the imaging catheter and a repair cartridge slidably disposed in the deployment catheter can be used to capture the target tissue and deploy a repair device into the tissue after proper capture is confirmed. System elements can be selectively removed from and replaced within port to deploy additional repair devices while port maintains a seal while elements are and are not inserted.

An exchangeable system for heart valve repair includes a port adapted to span a wall of a patient's heart that includes a sealing portion that creates a seal between the interior and exterior of the heart. An imaging catheter including at least one imaging element is slidably insertable into the port. A deployment catheter carrying a deployment mechanism is slidably insertable into the imaging catheter and a repair cartridge at least partially carrying a repair device is slidably insertable into the deployment catheter. A removable locking mechanism can be selectively engaged with the system to prevent the imaging catheter from moving distally relative to the port and when not engaged the imaging catheter is free to slide distally relative to the port to access target tissue in the heart to capture the tissue with a jaw assembly. The imaging element confirms proper capture of the target tissue and the deployment catheter and repair cartridge function together to deploy a repair device into the tissue. The sealing portion prevents blood from escaping the heart through the port while allowing selection insertion and removal of the imaging catheter, deployment catheter and repair cartridge through the port while the heart of the patient is beating.

A method includes providing a heart valve repair system and instruction for repairing target tissue of a patient's beating heart with the system. System includes a port having a sealing element, an imaging catheter slidably received in the port, a deployment catheter slidably received in the imaging catheter, a repair cartridge at least partially carrying a repair device slidably received in the deployment catheter and a locking mechanism. The locking mechanism is first engaged with the imaging catheter such that the imaging catheter cannot be moved distally relative to the port and the system is inserted into the heart in the locked configuration to position the port in the heart wall. The removable locking mechanism is then disengaged and the imaging catheter can be slid distally relative to the port towards target tissue to be repaired. The tissue is captured between the repair cartridge and at least one of the deployment catheter and imaging catheter and proper capture is confirmed with an imaging element in the imaging catheter. A repair device is then deployed into the captured target tissue with the deployment catheter and repair cartridge. The imaging catheter, deployment catheter and/or repair cartridge can then be selectively withdrawn and replaced to deploy additional repair devices as desired with the port maintaining a seal between the interior and exterior of the heart.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE FIGURES

The invention may be more completely understood in consideration of the following detailed description of various embodiments of the invention in connection with the accompanying drawings, in which:

FIG. 5 is a partial side view of a heart valve repair system according to an embodiment of the present invention.

Figure 1A:
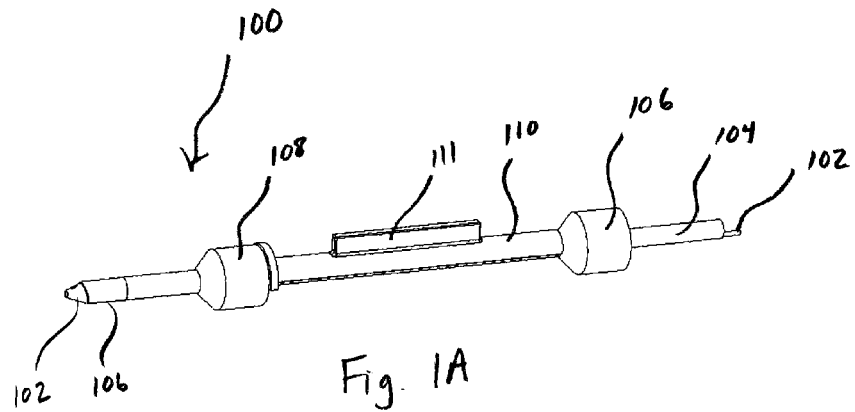
FIG. 1A is a perspective view of a heart valve repair system according to an embodiment of the present invention.
Figure 1B:
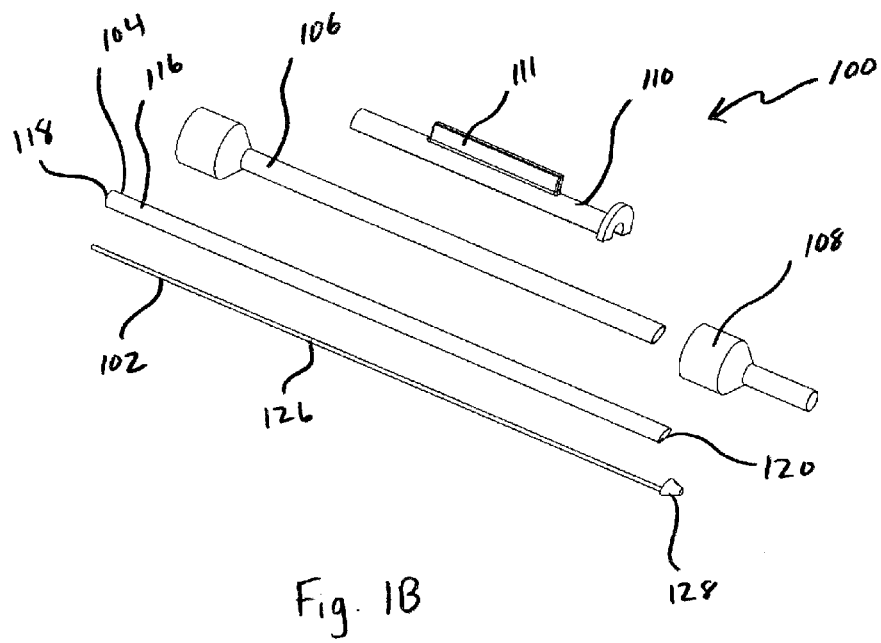
FIG. 1B is an exploded view of the heart valve repair system of FIG. 1A.
Figure 1C:
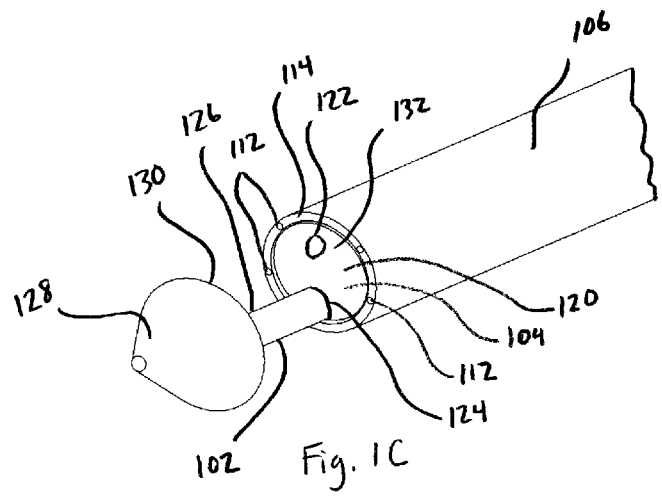
FIG. 1C is a partial view of the heart valve repair system of FIG. 1A.
Figure 1D:
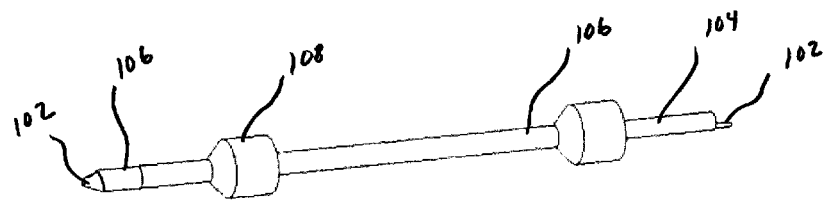
FIG. 1D is a perspective view of the heart valve repair system of FIG. 1A.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Embodiments of the present invention define a system that provides access into a heart chamber to repair a heart valve or other tissue structure while the heart is still beating and while minimizing the loss of blood with and without the system inserted. In one embodiment, the heart chamber is accessed transapically via thoracotomy followed by a ventriculotomy. The heart apex can initially be visualized directly through the thoracotomy or can be captured with a capture funnel which expands/unfolds until generally shaped like a conical funnel used to center, hold, and isolate the heart apex for incision. In other embodiments, the apex is visualized via an Ultrasound or IVUS system or via any other non-invasive imaging technique, such as, for example, fluoroscopy or magnetic or radio-frequency tracking.

Once access into the heart chamber is achieved, the system is navigatable via a non-invasive imaging modality. The system provides for capture of intra-cardiac tissue structure. Once captured, the system allows control to be maintained over said tissue structure. Using a device-based imaging component, the system allows confirmation of proper capture position of the system relative to the tissue structure. The system then accommodates the delivery of a repair device to said tissue structure to reduce/eliminate mitral valve regurgitation or other defect once proper position has been confirmed. Tissue structure, as used herein, can refer to any intracardiac structure that is a site for repair or anchoring, such as, for example, valve leaflets, papillary muscles or the heart wall. A repair device is any device whose function is to repair or replace a tissue structure, such as, for example, a suture.

An exchangeable heart valve repair system 100 for accomplishing the above described procedure is depicted in FIGS. 1A-1D. System 100 includes a suture cartridge 102 or other repair device, a deployment catheter 104, a fiber optic shaft 106, a port 108 and a locking mechanism 110. Fiber optic shaft 106 can communicate with a display (not pictured). A handle for guiding the device can be connected to a proximal end of system.

The fiber optic shaft or imaging catheter 106 comprises an elongate shaft that can contain device-based imaging, such as fiber optics or sensors. In one embodiment, fiber optics are carried within dedicated lumens 112 in an outer wall 114 of fiber optic shaft 106. Device based imaging can transmit an image to display that is used to confirm proper position on the tissue structure. In one embodiment, display will confirm whether there is full (proper) or partial or no (improper) tissue structure capture. Fiber optic shaft 106 also defines a lumen that allows passage of the deployment catheter 104.

Fiber optic shaft 106, also referred to more generally as an imaging catheter, can comprise individual optical fibers, bundled, within the wall thickness 114 and terminating flush at the distal tip of the catheter 106. In one embodiment, the optical fibers are evenly spaced around the circumference of the imaging catheter 106. In another embodiment, the optic fibers 106 are evenly spaced around the "top" semicircular arc of the catheter 106 relative to the suture cartridge 102. Device-based imaging can include one or more of, but is not limited to, fiber optics, a scope, ICE, OCT, Opto/Acoustic, IVUS, infrared and sonar. In one embodiment, system 100 does not employ a device-based imaging component.

The deployment catheter 104 is used to position and deploy a repair device, such as a suture, to the tissue structure, such as a valve leaflet. The deployment catheter 104 includes a shaft 116 having a proximal end 118 and a distal end 120 which is inserted into the lumen of the fiber optic shaft 106. The deployment catheter 104 can have an interference fit in the lumen of the fiber optic shaft 106 in order to retain the catheter 104 within the shaft 106 during the procedure. Alternatively, the lumen of the fiber optic shaft 106 can include a rib or other structure over which the deployment catheter 104 is advanced to provide a snap fit holding the catheter 104 within the shaft 106. A deployment mechanism such as a needle is slidably disposed in a needle lumen 122 extending through deployment catheter 104 for penetrating the valve leaflet to insert a suture. The deployment catheter 104 also includes a cartridge lumen 124 adapted to slidably contain the suture cartridge 102.

The suture cartridge 102 is loaded into the cartridge lumen 124 of deployment catheter 104 and forms a part of the deployment catheter 104. Suture cartridge 102 includes a shaft 126 and a tip 128. The suture cartridge 102 can contain some or all of a suture or other repair device used to repair tissue. The suture cartridge 102 and deployment catheter 104 operate together to form clamping jaws for grasping tissue such as a valve leaflet therebetween. Tip 128 of suture cartridge 102 is movable relative to deployment catheter 104 by sliding the suture cartridge 102 within the cartridge lumen 124 of deployment catheter 104. A proximally facing surface 130 of the tip 128 and a distally facing surface 132 of the deployment catheter 104 each operate as a portion of the clamping jaws for grasping tissue therebetween. Once tissue is grasped between the jaws, the repair device can be deployed with the deployment mechanism, such as by a needle penetrating the tissue to insert a suture. Details of various embodiments relating to tissue capture and repair device deployment are disclosed in PCT Pub. No. WO 2006/078694 A2 to Speziali and U.S. Patent Application Publication Nos. 2009/0105751 and 2009/0105729 to Zentgraf, each of which is hereby incorporated by reference.

Figure 2A:
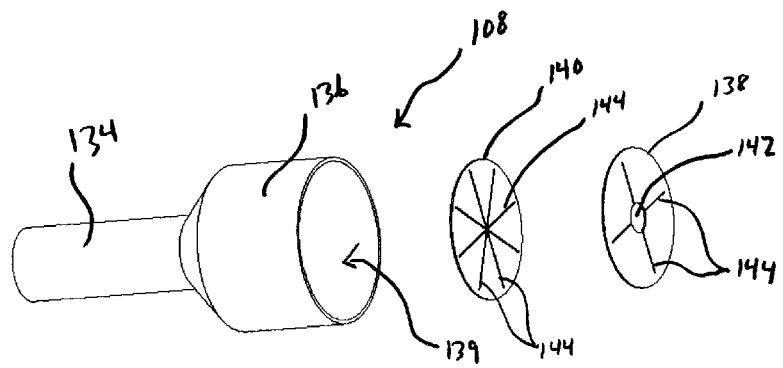
FIG. 2A is an exploded view of a port for a heart valve repair system according to an embodiment of the present invention.
Figure 2B:
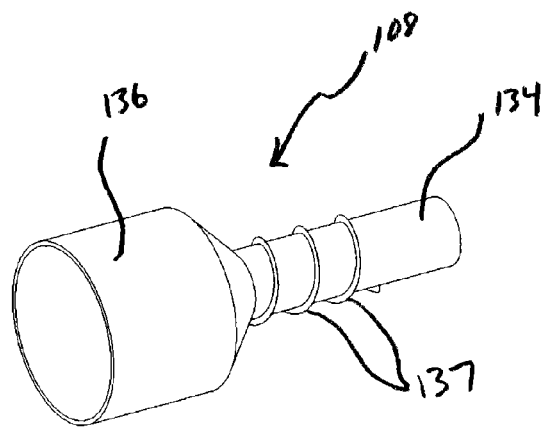
FIG. 2B is a perspective view of a port for a heart valve repair system according to an embodiment of the present invention.
Figure 2C:
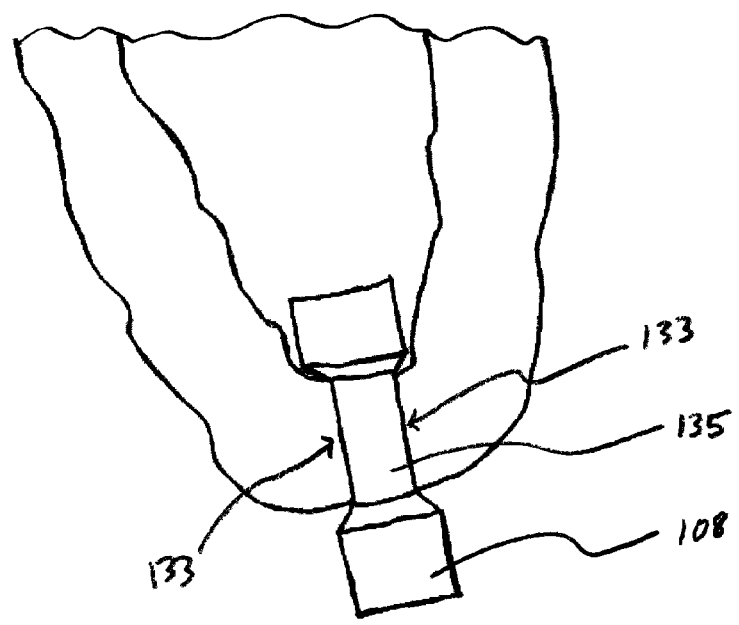
FIG. 2C is a perspective view of a port for a heart valve repair system according to an embodiment of the present invention.
Figure 2D:
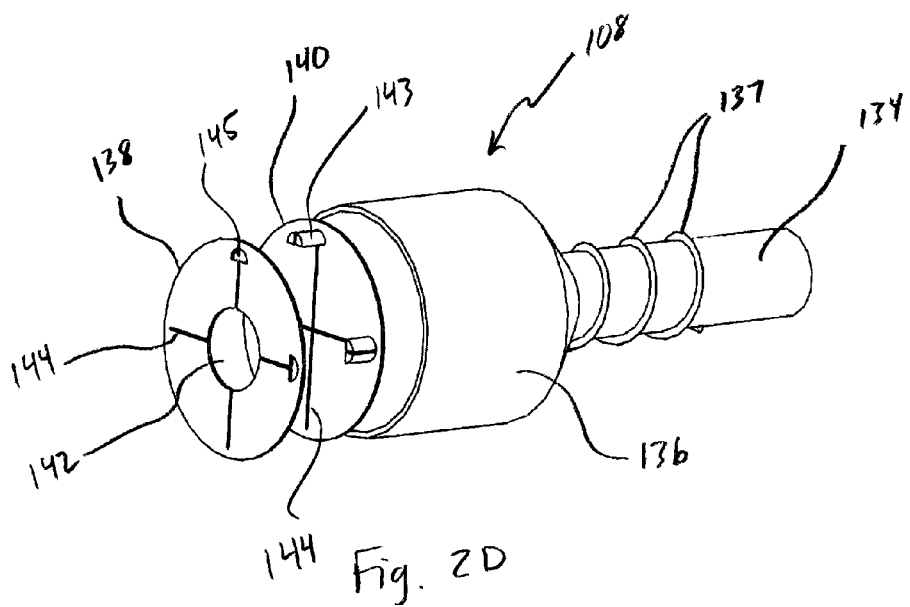
FIG. 2D is an exploded view of a port for a heart valve repair system according to an embodiment of the present invention.
Figure 2E:
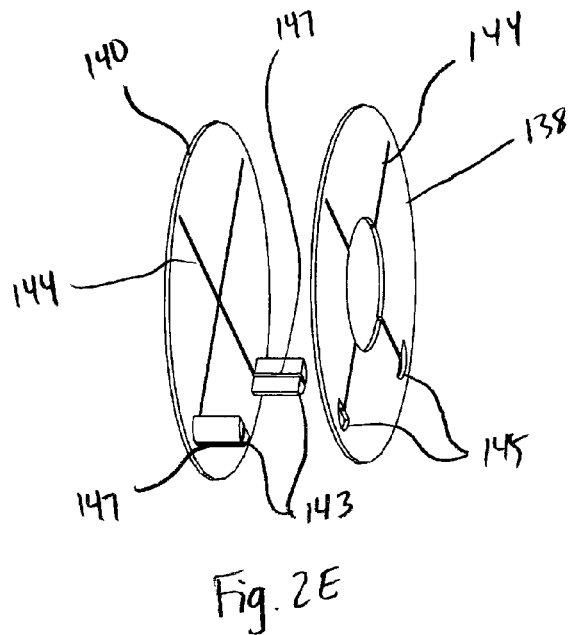
FIG. 2E is a perspective view of a portion of the port of FIG. 2D.

The port 108, shown in more detail in FIG. 2A, is positioned to span the heart muscle wall and is stabilized in that position during the procedure. Port 108 can include a stabilizing portion 134 and a sealing portion 136 and has an opening 139 extending through both portions between an interior and an exterior of the heart. In some embodiments, stabilizing portion 134 can include additional stabilizing structure, such as threads 137 as shown in FIG. 2B or ribs to increase stability of the port 108 in the heart wall. In an embodiment depicted in FIG. 2C, port 108 includes a circumferential groove 133 that defines a narrower central portion 135 around which the heart naturally constricts to provide further stability. In one embodiment, port 108 can comprise a soft material to allow the heart wall to compress into/around it to provide increased stabilization. Port 108 can be flexible to accommodate the insertion of pre-formed, canted shaft/tip shapes (e.g. shaped stylets) and other elements for the advancing/securing of knots (e.g. a knot pusher). Port 108 eliminates the need for multiple passes of the instrument directly against the heart muscle, minimizes blood loss due to instrument leakage and reduces push/pull forces on the heart wall. In an alternative embodiment, system 100 does not employ a port 108.

Port 108 can include one or more seals 138, 140 in sealing portion 136 to maintain hemostatasis with and without an instrument inserted to allow multiple exchanges of tools in the heart chamber while minimizing blood loss. A first seal 138 can include an opening 142 designed to seal around an inserted instrument to maintain hemostasis with the instrument inserted. In one embodiment, the opening 142 is oblong to accommodate a shaft of a similarly shaped instrument. In another embodiment, the opening 142 is symmetrically circular to accommodate an instrument with a shaft of a matching shape. Such a configuration allows the instrument to be circumferentially rotated following insertion. A second seal 140 can be used to maintain hemostasis when no instrument is inserted. Seals 138, 140 can include slits 144. In addition to allowing an instrument to pass through the seals 138, 140, each slit 144 can secure a suture or similar repair device and hold it out of the way of the procedure while also limiting risk of unintentional tension exerted onto the suture. When multiple sutures are inserted, each can be held in a slit 144 to prevent tangling of the sutures with each other or on successive passes of the instrument. In one embodiment, seal 140 can include suture retention projections 143 that include suture grooves 147 that can extend partially or completely through projections 143 for enhanced suture retention. In such an embodiment, seal 138 can include apertures 145 for accommodating suture retention projections 143. The system 100 can therefore control and accommodate multiple deployed repair devices from interfering with the subsequent deployment of more repair devices. In one embodiment, the seals 138, 140 are fixed in place relative to port 108. In another embodiment, the seals 138, 140 are free to rotate and/or move linearly within sealing portion 136.

A handle can be connected to a proximal end of the device 100 to allow control over the device position, jaw actuation, and repair device deployment. In one embodiment, each deployment catheter 104 and/or suture cartridge 102 includes a separate handle that is removed and exchanged when the catheter 104 or cartridge 102 is removed. In another embodiment, the system 100 includes a single handle to which multiple deployment catheters 104 or suture cartridges 102 are exchangeable and attachable. Handle can provide for manual or automatic actuation of the deployment mechanism for the repair device.

A display can be communicatively coupled to the system to receive the images and/or other information captured by device-based imaging. In one embodiment, a cable connects the fiber optic shaft 106 and display. In another embodiment, display wirelessly communicates with the system 100 to obtain the observed data. Display can be an integrated display of system or standard OR monitors. An integrated display can be included as part of the handle. Alternatively, display can be projected onto a location convenient for the physician (e.g. wall, head-up display, etc.). In some embodiments, display can provide, in addition to or in lieu of visual feedback, auditory or tactile feedback.

The removable locking mechanism 110 locks the port 108 and fiber optic shaft or imaging catheter 106 relative to each other, which holds the tip 128 and the fiber optic shaft 106 in proper position for penetration into the heart muscle. Thus, as force is exerted by the physician from a proximal end of the system 100 into the heart wall with the distal end of the system 100, the suture cartridge 102, deployment catheter 104, fiber optic shaft 106 and port 108 remain stationary with respect to each other as the heart is penetrated and the device remains stiff to allow insertion into the heart. In one embodiment, removable locking mechanism 110 holds the components in place via an interference fit. In another embodiment, removable locking mechanism 110 utilizes a snap fit. When removable locking mechanism 110 is removed, as in FIG. 1D, fiber optic shaft 106 (and with it deployment catheter 104 and suture cartridge 102) are able to slide forwardly relative to port 108 in order to access the repair site. In one embodiment, removable locking mechanism 110 is rigid.

Removable locking mechanism 110 can include a projection or fin 111 that aids in removal of locking mechanism 110. In one embodiment, fin 111 is rigid and unitary with locking mechanism 110. Alternatively, fin 11 can be retractable via, for example, a spring mechanism to reduce the profile of locking mechanism 110 when desired. In other embodiments, removable locking mechanism 110 can be removable with a separate removal tool, such as a magnetic removal tool that cooperates with a magnet in locking mechanism 110 or a removal tool that is keyed to fit into and mate with a recess in locking mechanism. The length of locking mechanism 110 can be used to control a distance that the imaging catheter 116 and tip 128 extend from the port 108 during insertion. Typically, it is desirable to minimize this distance.

Figure 6:
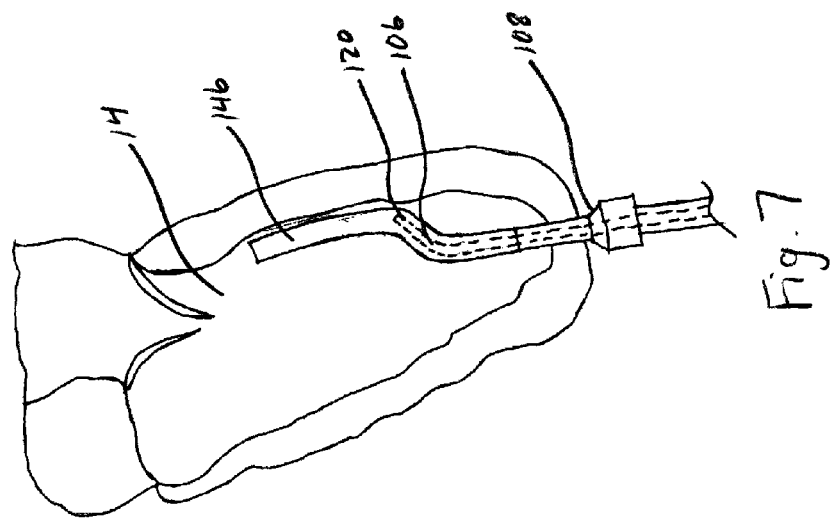
FIG. 6 is a schematic representation of a step in a method of repairing a heart valve according to an embodiment of the present invention.
Figure 7:
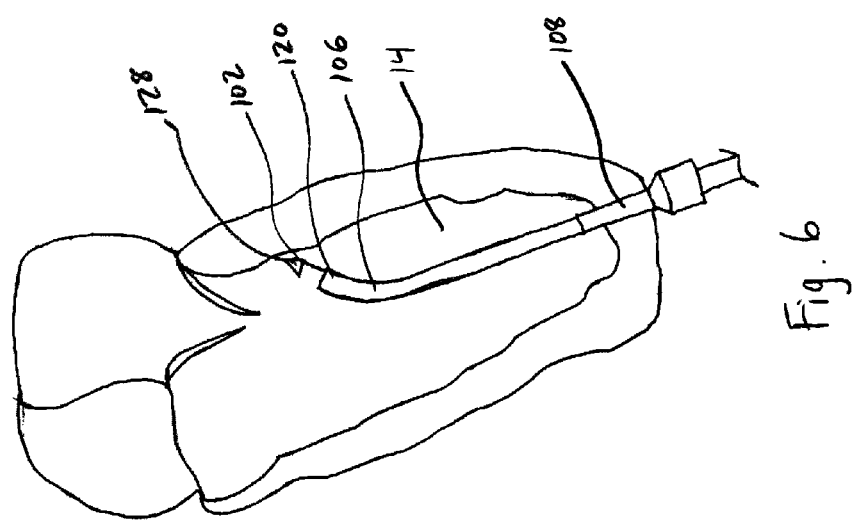
FIG. 7 is a schematic representation of a step in a method of repairing a heart valve according to an embodiment of the present invention.
Figure 8:
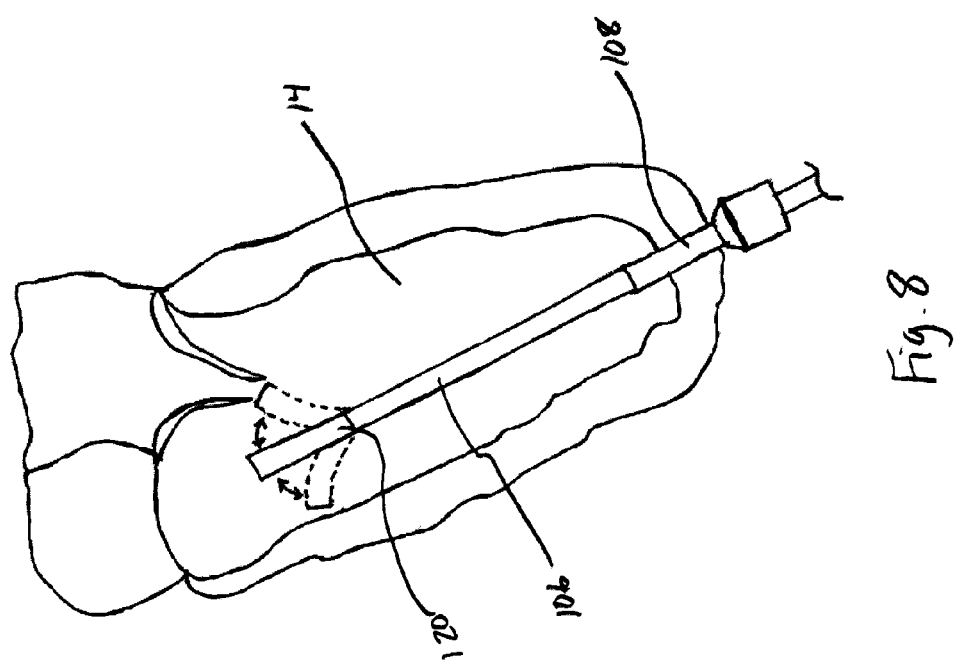
FIG. 8 is a schematic representation of a step in a method of repairing a heart valve according to an embodiment of the present invention.

In one embodiment, tip 128 of suture cartridge 102 is provided with a tapered configuration in order to ease entrance through and dilate the opening in the heart wall. Such a configuration reduces the insertion force necessary for entrance into the heart wall and the port 108. Alternatively, system 100 can employ a separate trocar to penetrate the incision and seat port 109, which is then removed and replaced with imaging catheter 106. In one embodiment, tip 128 and shaft 126 of suture cartridge 102 and distal end 120 of fiber optic shaft 106 and deployment catheter 104 extend generally straight outwardly from system 100 as shown in FIG. 5. In another embodiment, distal end 120 has a preformed and permanent curve to allow access to difficult and hard to reach areas of the heart chamber 14 as shown in FIG. 6. Distal end 120 can also be flexible as shown in FIG. 7 to allow it to conform to the shape of pre-formed stylets 146 to guide fiber optic shaft 106 and deployment catheter 104 along a pre-defined path. In a further embodiment, distal end 120 can be capable of articulating between various angular positions as shown in FIG. 8 to allow it to adapt to various insertion geometries.

Figure 3:
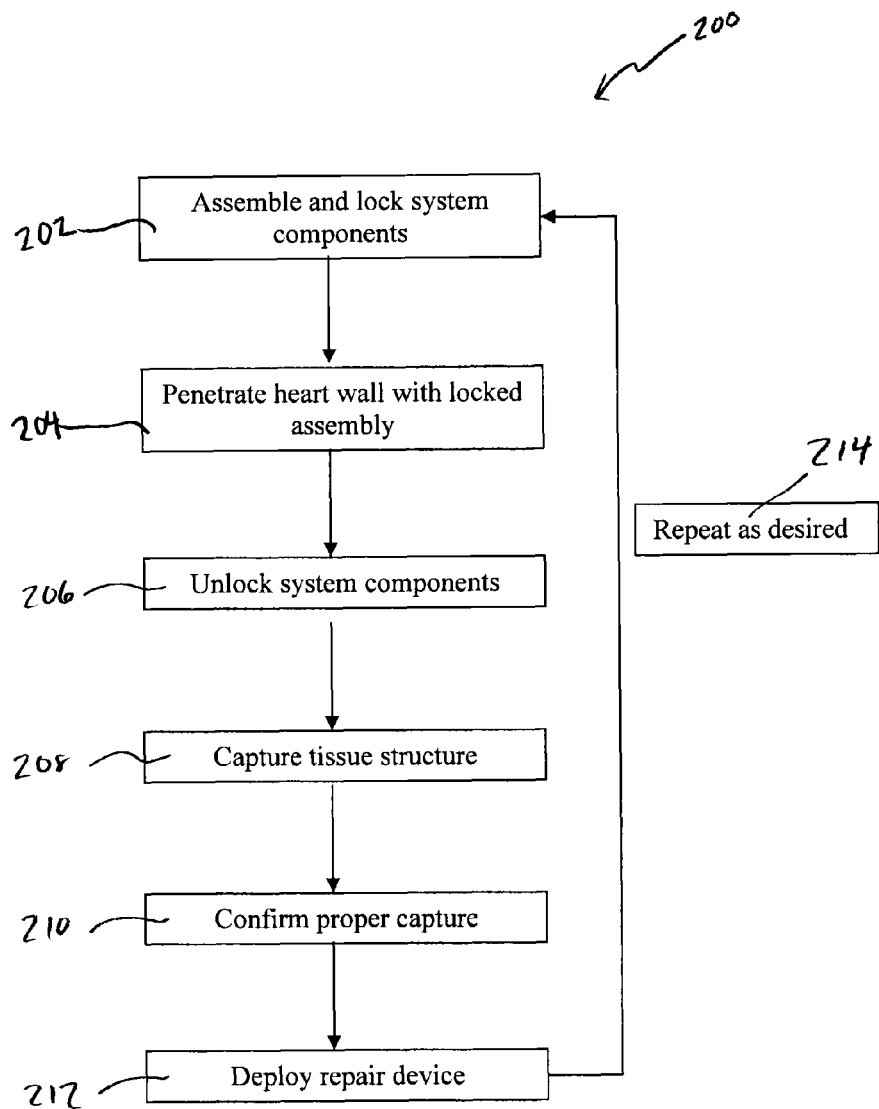
FIG. 3 is a flowchart of steps in a method of repairing a heart valve according to an embodiment of the present invention.
Figure 4B:
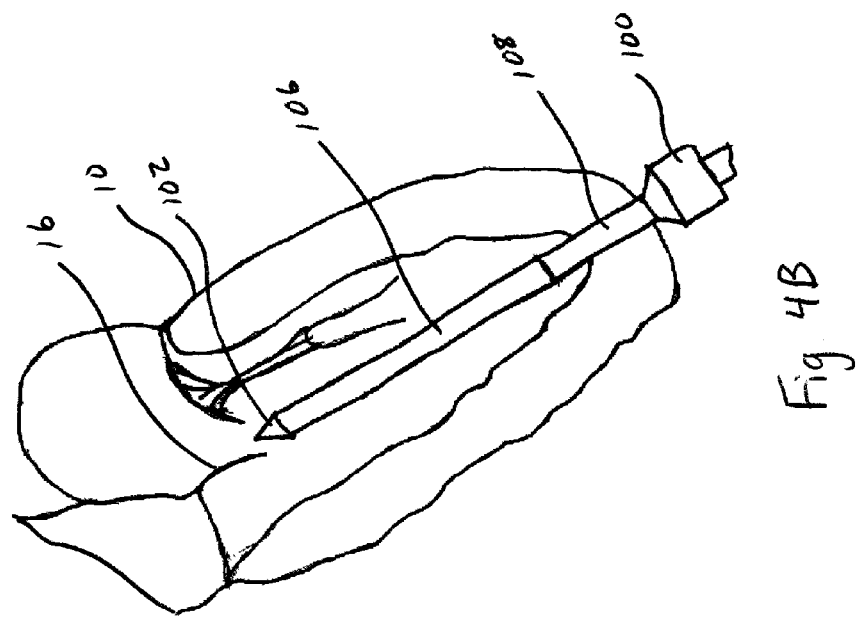
FIG. 4B is a schematic representation of a step in a method of repairing a heart valve according to an embodiment of the present invention.
Figure 4A:
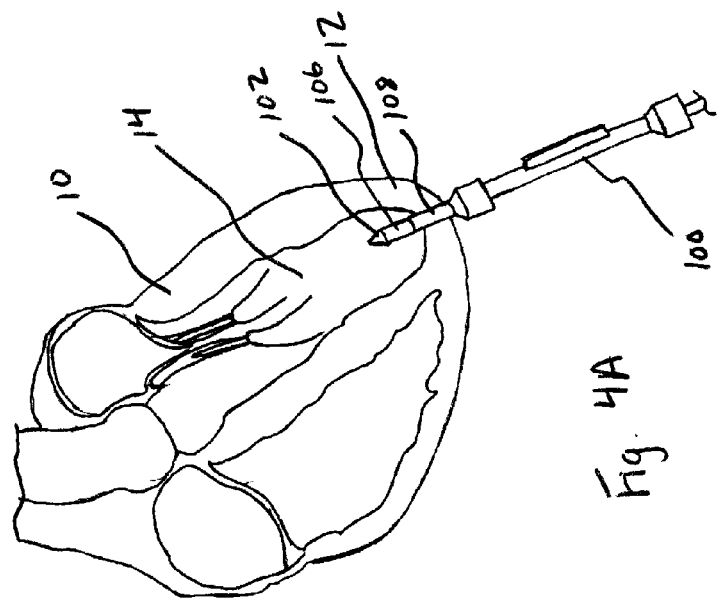
FIG. 4A is a schematic representation of a step in a method of repairing a heart valve according to an embodiment of the present invention.

The flowchart depicted in FIG. 3 shows the steps of a surgical procedure 200 utilizing exchangeable repair system 100 according to an embodiment of the present invention. In preparation for the initial insertion of the system into the heart chamber, the components are assembled and removable locking mechanism locks the fiber optic shaft 106 and port 108 in place relative to each other at step 202. The locked assembly is then advanced as a unit penetrating into the heart 10 through a heart wall 12 and into a heart chamber 14 at step 204 as shown in FIG. 4A. The left ventricle is accessed via port 108 to facilitate entrance of the system 100 into the heart chamber. The lock is then removed at step 206 to allow the fiber optic shaft 106 to slide relative to the port 108 as needed.

The cartridge 102 slides in a dedicated lumen 124 inside of the deployment catheter 104. The deployment catheter 104 can slide in a dedicated lumen inside of the fiber optic shaft 106, but can remain generally in place during the procedure due to an interference fit or other structure retaining the deployment catheter 104 in the fiber optic shaft 106. The fiber optic shaft 106 slides in a dedicated lumen inside of the port 108. The port 108 maintains the access into the heart chamber 14 and remains seated in the heart wall 12 as the other components are selectively moved relative to the port 108. At step 208, the deployment catheter 104, suture cartridge 102 and fiber optic shaft 106 can be advanced to a tissue structure 16 to capture the tissue structure 16 with the clamping jaws. Device-based imaging present in the fiber optic shaft 106 is used to confirm proper tissue capture at step 210. A repair device, such as a suture, can be deployed onto the tissue at step 212. The deployment catheter 104 and/or suture cartridge 102 can then be removed and a new deployment catheter 104, suture cartridge 102 or other repair device can be inserted a desired number of times to deploy additional repair devices at step 214. The deployment catheter 104 can be exchanged with or without the fiber optic shaft 106. Tools having various functions and/or employing various repair devices can be used interchangeably with system 100 by insertion into fiber optic shaft 106.

In one embodiment, the port 108 has an inner diameter of approximately 32 french, the fiber optic shaft has an outer diameter of 28 french, the deployment cather has an outer diameter of 24 french, and the repair cartridge 102 shaft 126 has an outer diameter of 5 french. The removable locking mechanism can have a height of about 5 french.

System 100 can be utilized in conjunction with non-invasive imaging distinct from the device-based imaging for confirmation capture in order to further enhance visualization and positioning of the system inside the heart. Non-invasive imaging refers to imaging modalities that are independent of the device and are used for global navigation of the device inside the heart. In one embodiment, the system 100 can be guided when inside the heart via TEE (Transesophageal Echo—2D and 3D). In another embodiment, the system 100 is guided via real-time MRI. In other embodiments, the system 100 can be guided using fluoroscopy, infrared or sonar. In an embodiment, no external non-invasive imaging is needed.

Device-based imaging is used by system 100 to precisely locate the deployment catheter 104 and fiber optic shaft or imaging catheter 106 on the target zone of the tissue structure. Device-based imaging can be carried by a separate fiber optic shaft or independent imaging catheter 106 or be incorporated into the deployment catheter 104.

Figure 9:
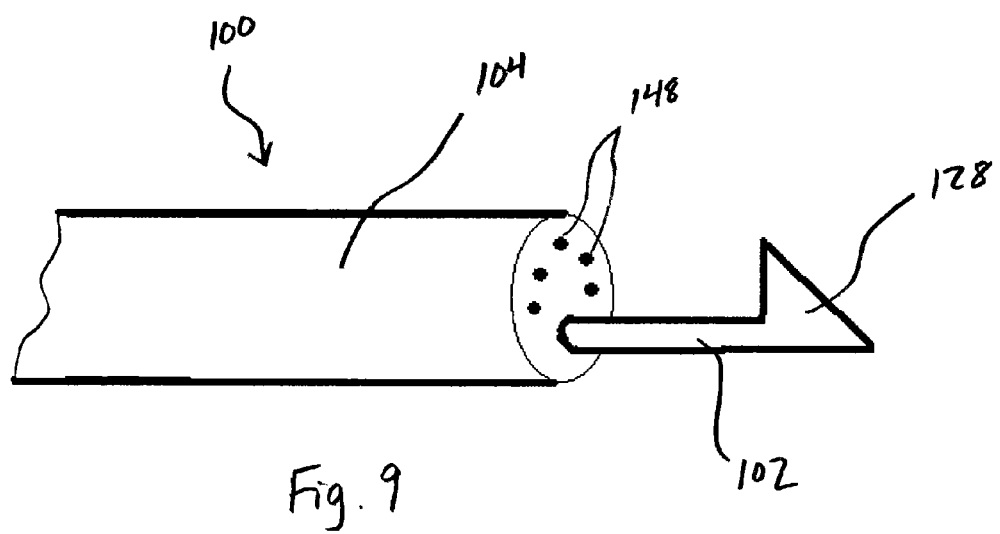
FIG. 9 is a partial side view of a heart valve repair system according to an embodiment of the present invention.

In one embodiment, the device-based imaging is integrated into the deployment catheter 104 via a plurality of channels 148 carrying imaging elements to the distal end of the catheter as shown in FIG. 9. Capture of the tissue structure simultaneously results in indication of proper capture. When proper capture has been achieved, the repair device can be deployed.

Figure 10A:
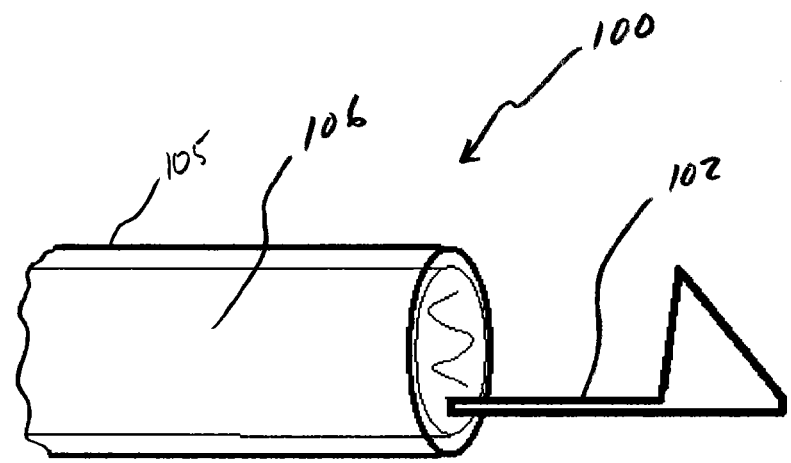
FIG. 10A is a partial side view of a heart valve repair system according to an embodiment of the present invention.
Figure 10B:
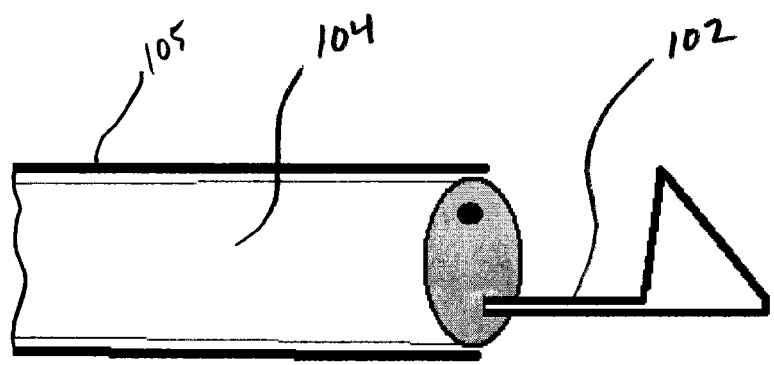
FIG. 10B is a partial side view of a heart valve repair system according to an embodiment of the present invention.
Figure 11:
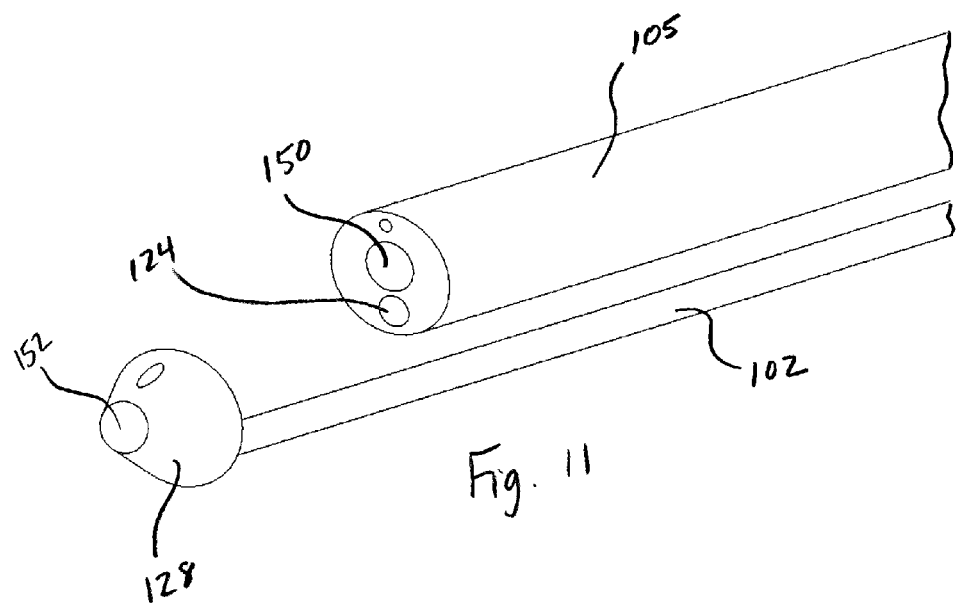
FIG. 11 is a partial perspective view of a heart valve repair system according to an embodiment of the present invention.

In other embodiments, the device-based imaging is independent of the deployment catheter 104. One embodiment is depicted in FIGS. 10A and 10B. The system 100 is inserted into the heart chamber with the independent imaging catheter or fiber optic shaft 106 inserted comprising the proximal face of the clamp that is formed with the suture cartridge 102. Capture of the tissue structure simultaneously results in indication of proper capture. When proper capture has been achieved, the independent imaging catheter 106 is retracted (intermediate proximal clamp surface may be used or the outer sheath 105 may be used to maintain control of the tissue structure). The deployment catheter 104 is then inserted and the repair device can be deployed. FIG. 11 depicts an additional embodiment wherein a deployment sheath 105 defines a lumen 124 for the suture cartridge 102 and a separate lumen 150 that can separately carry the imaging catheter 106 and the deployment catheter 104 carrying the repair device. Suture cartridge 102 can include an opening 152 to enhance visualization through tip 128. In some embodiments, following deployment of the repair device, the deployment catheter 104 can be removed and the imaging catheter 106 reinserted to visualize/confirm effectiveness of the deployed repair device. In an embodiment, the same independent imaging catheter and deployment catheter can be reused wherein said deployment catheter is reloaded with new repair devices. In a further embodiment, the deployment catheter is disposable after a single use. Each new repair device is then loaded in a new deployment catheter.

Figure 12:
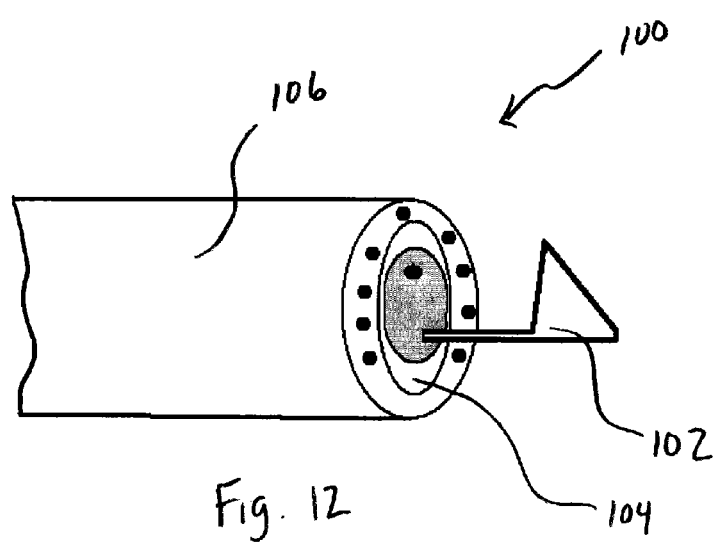
FIG. 12 is a partial side view of a heart valve repair system according to an embodiment of the present invention.

Device-based imaging can also be linked to the deployment catheter 104 as described previously herein with reference to FIGS. 1A-1D and as further illustrated in FIG. 12. The system 100 enters the heart chamber with the linked imaging catheter 106 inserted comprising the proximal face of the clamp. The linked imaging catheter 106 and port 108 are locked together for puncture access into the heart chamber. The system can then be unlocked allowing the imaging catheter 106 to move independently in and out of the port 108. Capture of the tissue structure simultaneously results in indication of proper capture. When proper capture has been achieved, the repair device can be deployed. The deployment catheter 104 can be retracted leaving the linked imaging catheter 106 in place. The linked imaging catheter 106 and deployment catheter 104 can also be removed together as one. Multiple repair devices can be deployed in this manner with the port 108 maintaining a seal and allowing different repair devices to be deployed. In one embodiment, the same deployment catheter 104 can be reused by being reloaded with new repair devices. In another embodiment, the deployment catheter 104 is disposable after a single use and each new repair device is loaded in an individual deployment catheter 104.

Figure 15:
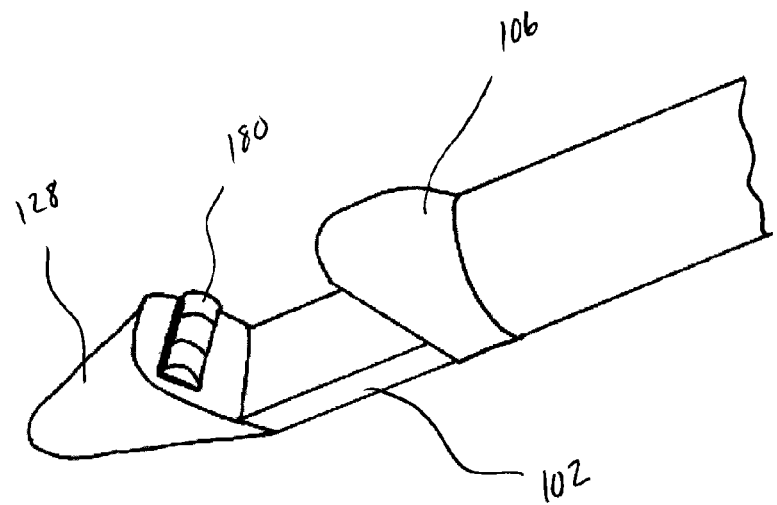
FIG. 15 is a partial perspective view of a portion of a heart valve repair system according to an embodiment of the present invention.

In another embodiment of the deployment catheter 104 and cartridge 102 tip 128, multiple sets of clamps may be used, e.g., a secondary clamp composed of a retractable/collapsible wire form can be used for gross capture of the tissue structure and a primary clamp can then be used for finer precision. The primary clamp can be positioned and repositioned as desired while the secondary clamp prevents total loss of control of the tissue structure. In another embodiment shown in FIG. 15, a single clamp can incorporate a rolling mechanism 180. Said mechanism can be spring loaded, or loaded in a similar fashion, such that as the clamps are opened to reposition, the rolling mechanism protrudes, keeping contact/control of the tissue structure, but allowing repositioning. As the clamps are closed, the rolling mechanism is retracted into the tip 128 and does not interfere with clamp closure.

Figure 14:
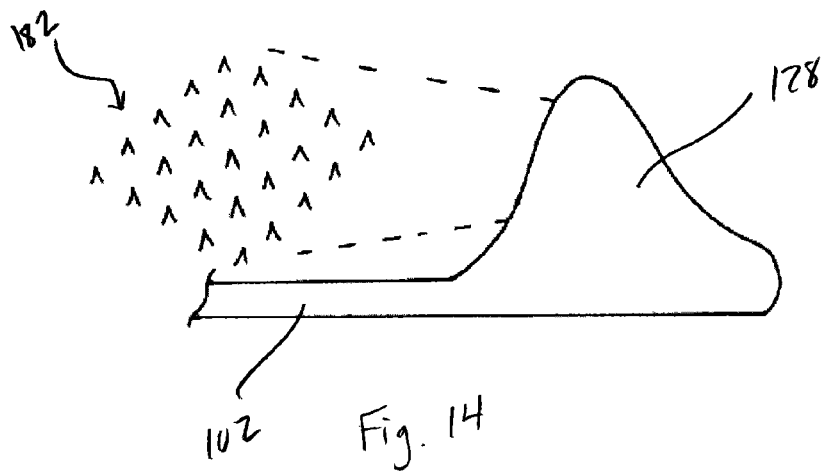
FIG. 14 is a schematic representation of a portion of a heart valve repair system according to an embodiment of the present invention.

In one embodiment shown in FIG. 14, the clamp face of tip 128 and/or deployment catheter 104 is embedded with microneedles 182 for drug delivery. The drug delivered could aid in tissue growth on/through the repair device. The drug could also alter the composition of the leaflet, such as by tightening the leaflet to reduce mitral valve regurgitation (such that the drug acts as the repair device).

System 100 can be designed to load and deploy a single repair device. Alternatively, multiple repair devices can be loaded at one time and deployed simultaneously or in series. In such an embodiment, multiple repair devices can be deployed without withdrawing the deployment catheter 104 far away from the target or out of the heart completely. In one embodiment, the deployment action of a first repair device is linked to the loading action of a second repair device. In some embodiments, multiple sutures can be used on the same leaflet. Multiple sutures on both leaflets can be used and tethered together to create an edge-to-edge repair.

The repair device delivered by the system can be a suture that is delivered through the leaflet and secured with a girth hitch knot. The suture can then be tensioned to reduce mitral valve regurgitation and anchored to the exterior of the heart apex. The suture can alternatively be anchored to the papillary muscle, to the heart wall (i.e., more lateral relative to the apex) or to a leaflet of another heart valve (e.g., a mitral valve leaflet tethered to an aortic valve leaflet). Alternatively, other securing methods can be used including alternative knots, use of a knot pusher, the creation and advancement of the knot from the exterior of the heart, the creation/advancement of the knot while inside the heart chamber, and the use of an attachment clip.

The suture can be captured by a deployment mechanism (e.g. a hooked needle) with a single capture area. In another embodiment, a deployment mechanism can have redundant capture points (e.g. a needle with multiple hooks or a corkscrew shape). In a further embodiment, a key and lock mechanism can be used wherein the deployment mechanism locks into a key mechanism that is connected to the suture. Alternatively, the suture is used to capture the deployment mechanism (e.g. the suture is held open in a lasso formation, the hook is passed through, the lasso is closed around the hook, and then the hook is retracted). In one embodiment, the deployment mechanism can have a retractable/collapsible capture end (e.g. the tip closes similar to an umbrella and the tip is passed by the suture in the closed position, opened, retracted to the suture, and closed around the suture).

Figures 13A, 13B:
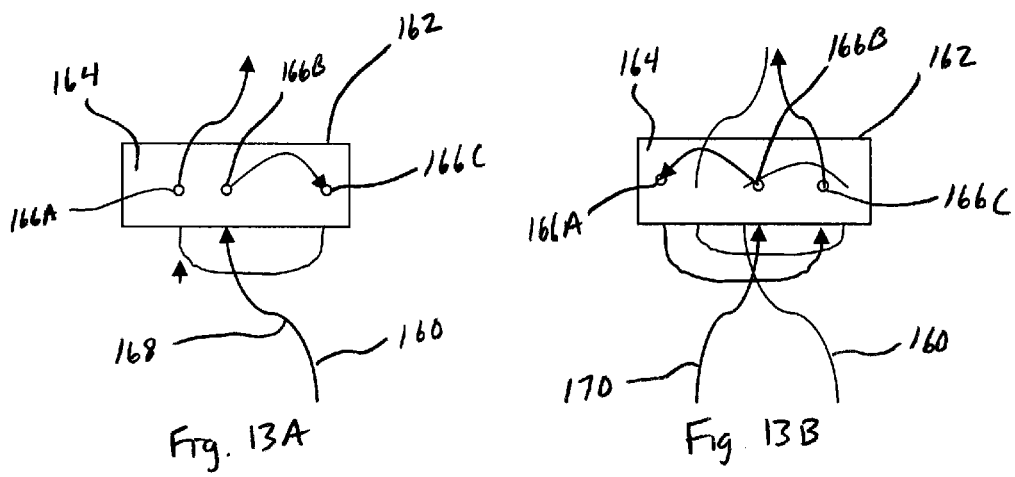
FIG. 13A is a top view of a portion of a heart valve repair system according to an embodiment of the present invention.
FIG. 13B is a top view of the portion of a heart valve repair system of FIG. 13A.
Figures 13C, 13D:
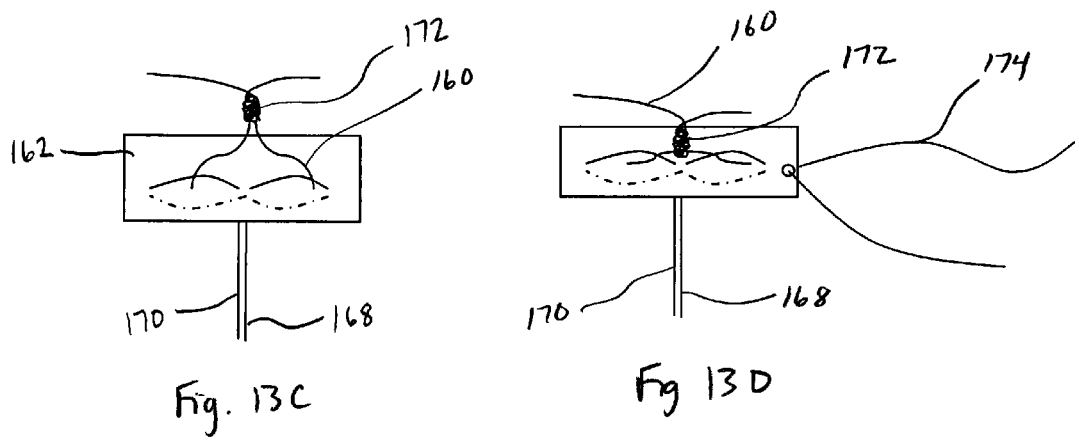
FIG. 13C is a top view of the portion of a heart valve repair system of FIG. 13A.
FIG. 13D is a top view of the portion of a heart valve repair system of FIG. 13A.

In some embodiments, sutures 160 can be anchored with the use of a pledget 162 as shown in FIGS. 13A-13D. Pledgets 162 typically comprise a thin soft material, such as, for example, teflon. Pledget 162 defines a body 164 having one or more apertures 166 extending through body 164. In one embodiment, pledget 162 has three apertures 166A, 166B, 166C. Following deployment of the suture 160 onto a tissue structure, a first free end 168 and a second free end 170 of the suture can be passed through the pledget apertures 166A-C. In one embodiment, free ends 168, 170 are passed through pledget 162 as shown in FIGS. 13A and 13B in the direction and order indicated by the arrows. First free end 168 of suture 160 is threaded up through second aperture 166B, down through third aperture 166C and then back up through first aperture 166A. Second free end 170 is also threaded up through second aperture 166B and then down through first aperture 166A and back up through third aperture 166C. Free ends 168, 170 can then be used to form a knot 172 as shown in FIG. 13C. In one embodiment, pledget 162 does not have apertures 166 and instead suture 160 is threaded through pledget with a needle or other penetrating device. A retrieval suture 174 that can be comprised of, for example, prolene, can then be threaded through the pledget 162 as shown in FIG. 13D. The pledget 162 and suture 160 can be inserted into the heart chamber by using a blunt end forceps or similar instrument to pass the knot 172 into the chamber approximately mid-way to the valve. Once in the chamber, the knot 172 can be released and the suture 160 and pledget 162 can be delivered to the tissue structure by pulling on the loop end of the suture 160. In one embodiment, multiple sutures on one or both leaflets can be tied to the same pledget 162.

Port 108 can include additional features to aid in use of a pledget 162 or other repair device. Port 108 can include structure that moves and holds tissue structures, such as muscle, tendinae and connective tissue, at the insertion point out of the way to ease insertion of a repair device well into the open space of the heart chamber to limit snagging of the repair device on the tissue during insertion. Alternatively, port 108 can include an insertion channel that extends well into the heart chamber to allow the repair device to be inserted into the open area of the heart beyond said tissue. In addition, port 108 can utilize structure to aid in retrieving and removing a repair device to limit interference with retrieval of the device back out of the heart chamber.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A system for repairing a heart valve in a beating heart of a patient, comprising:
   a port adapted to span a wall of the heart of the patient, the port having an opening extending therethrough and including a sealing portion including at least one seal configured to be positioned in the opening between an interior and an exterior of the heart;
   an imaging catheter slidably insertable into the opening of the port, the imaging catheter having at least one lumen therethrough and including at least one imaging element;
   a deployment catheter slidably insertable into the at least one lumen of the imaging catheter, the deployment catheter carrying a deployment mechanism and including at least one lumen therethrough, wherein a distal end of at least one of the imaging catheter and the deployment catheter forms a first portion of a jaw assembly for grasping target tissue for repair in the heart;
   a repair cartridge slidably insertable into the lumen of the deployment catheter, the repair cartridge at least partially carrying a repair device adapted to repair the target tissue that is deployed onto the target tissue in conjunction with the deployment mechanism, the repair cartridge having a shaft with a tip at a distal end of the shaft, and wherein a proximally facing surface of the tip forms a second portion of the jaw assembly; and
   an elongate removable locking mechanism selectively removable from contact with both the imaging catheter and the port and configured to engage the imaging catheter longitudinally along a length of an outer circumferential surface of the imaging catheter to prevent the imaging catheter from moving distally towards the target tissue relative to the port when the removable locking mechanism is engaged with the imaging catheter and a proximal force is applied to the imaging catheter for inserting the imaging catheter into the heart of the patient, the removable locking mechanism configured to move together with the imaging catheter when engaged with the imaging catheter;
   wherein the imaging catheter is free to slide distally relative to the port to access the target tissue in the heart when the removable locking mechanism is not engaged with the imaging catheter to capture the target tissue with the jaw assembly;
   wherein the at least one imaging element confirms proper capture of the target tissue with the jaw assembly; and
   wherein the at least one seal substantially prevents blood from escaping the heart through the port while providing for selective insertion and removal of the imaging catheter, deployment catheter and repair cartridge through the port while the heart of the patient is beating.

2. The system of claim 1, further comprising a second repair cartridge at least partially carrying a second repair device, the second repair cartridge adapted to replace the repair cartridge in the system following deployment of the repair device.

3. The system of claim 2, further comprising a second deployment catheter, wherein the second repair cartridge is inserted into the second deployment catheter.

4. The system of claim 1, wherein the repair device is a suture.

5. The system of claim 4, further comprising a pledget to which the suture is attached following deployment of the suture, the pledget adapted to directly interface with the target tissue.

6. The system of claim 1, wherein the at least one imaging element comprises a plurality of fiber optics carried within at least one dedicated lumen in the imaging catheter.

7. The system of claim 1, wherein the removable locking mechanism engages an outer surface of the imaging catheter and prevents the imaging catheter from moving distally towards the target tissue by providing a physical barrier sandwiched between a proximal surface of the port and a distal surface of a portion of the imaging catheter that is raised relative to the outer surface of the imaging catheter with which the removable locking mechanism is engaged.

8. The system of claim 1, wherein the tip of the repair cartridge has a tapered distal end.

9. The system of claim 1, wherein the sealing portion of the port includes at least a first seal and a second seal, the first seal having an opening adapted to seal around an outer surface of the imaging catheter and the second seal having a plurality of slits that remain generally sealed when the imaging catheter is not inserted through the second seal.

10. The system of claim 1, wherein the port includes a stabilizing portion that is configured to engage with and seal with the heart wall and is configured to extend into the heart to provide access to the interior of the heart through the port.

11. A method of providing instruments and instructions for repairing a valve leaflet comprising:
    providing the device of claim 1; and
    providing instructions for operating the device of claim 1 to repair the valve leaflet.

12. A system for repairing a heart valve in a beating heart of a patient, comprising:
    a port adapted to span a wall of the heart of the patient, the port having an opening extending therethrough configured to be positioned between an interior and an exterior of the heart;
    a catheter slidably insertable into the opening of the port, the catheter including at least one imaging element and a deployment mechanism and having a distal end that forms a first portion of a jaw assembly adapted to grasp target tissue for repair in the heart;
    a repair cartridge slidably insertable into the catheter, the repair cartridge at least partially carrying a repair device that is deployed into the target tissue in conjunction with the deployment mechanism and having a shaft with a tip at a distal end of the shaft that forms a second portion of the jaw assembly, wherein the imaging element confirms proper capture of the target tissue with the jaw assembly;
    an elongate removable locking mechanism adapted to engage the catheter longitudinally along a length of an outer circumferential surface of the catheter to prevent the catheter from moving distally towards the target tissue relative to the port when the removable locking mechanism is engaged with the catheter and a proximal force is applied to the catheter for inserting the catheter into the heart of the patient, the removable locking mechanism configured to move together with the catheter when engaged with the catheter and the catheter being free to slide distally relative to the port to access the target tissue in the heart when the removable locking mechanism is not engaged with the catheter; and
    a seal positioned within the opening of the port, the seal adapted to substantially prevent blood from escaping the heart through the port while providing for selective insertion and removal of the catheter and repair cartridge through the port while the heart of the patient is beating.

13. The system of claim 12, wherein the catheter comprises an imaging catheter carrying the imaging element and a separate deployment catheter carrying the deployment mechanism.

14. The system of claim 13, wherein the deployment catheter is slidably insertable into a lumen of the imaging catheter.

15. The system of claim 13, wherein the deployment catheter and imaging catheter are selectively insertable into a common lumen in the catheter.

16. The system of claim 12, further comprising a second repair cartridge at least partially carrying a second repair device, the second repair cartridge adapted to replace the repair cartridge in the system following deployment of the repair device.

17. The system of claim 1, wherein the repair device is a suture.

18. The system of claim 17, further comprising a pledget to which the suture is attached following deployment of the suture, the pledget adapted to directly interface with the target tissue.

19. The system of claim 12, wherein the removable locking mechanism engages an outer surface of the catheter and prevents the catheter from moving distally towards the target tissue by providing a physical barrier sandwiched between a proximal surface of the port and a distal surface of a portion of the catheter that is raised relative to the outer surface of the catheter with which the removable locking mechanism is engaged.

20. The system of claim 12, wherein the at least one seal includes at least a first seal and a second seal, the first seal having an opening adapted to seal around an outer surface of the catheter and the second seal having a plurality of slits that remain generally sealed when the catheter is not inserted through the second seal.

21. A method of providing instruments and instructions for repairing a valve leaflet, comprising:

providing the device of claim 12; and providing instructions for operating the device of claim 19 to repair the valve leaflet.

\* \* \* \* \*